United States Patent [19]

Cushman

[11] 4,287,423

[45] Sep. 1, 1981

[54] PANORAMIC DENTAL RADIOGRAPHY IMAGE INTENSIFICATION EMPLOYING MINIFICATION TECHNIQUES

[75] Inventor: Robert H. Cushman, Princeton, N.J.

[73] Assignee: Pennwalt Corporation, Philadelphia, Pa.

[21] Appl. No.: 92,883

[22] Filed: Nov. 9, 1979

[51] Int. Cl.³ .................... G01N 23/00; G01T 1/00
[52] U.S. Cl. ............................. 250/439 P; 250/487
[58] Field of Search .................. 250/439 P, 320, 227, 250/321, 323, 487, 460, 213 VT; 355/1

[56] References Cited

U.S. PATENT DOCUMENTS

| | | | |
|---|---|---|---|
| 2,433,129 | 12/1947 | Land | 250/320 |
| 2,510,965 | 6/1950 | Draeger et al. | 250/320 |
| 3,448,276 | 6/1969 | Witte | 250/227 |
| 3,461,332 | 8/1969 | Sheldon | 250/213 VT |
| 4,015,126 | 3/1977 | Herrington | 250/320 |

FOREIGN PATENT DOCUMENTS 2203432  8/1973  Fed. Rep. of Germany .......... 250/320

OTHER PUBLICATIONS

Kapany, "Fiber Optics: Principles and Applications," Academic Press, N.Y., 1967, pp. 238-241.

*Primary Examiner*—Alfred E. Smith
*Assistant Examiner*—Carolyn E. Fields

[57] ABSTRACT

Panoramic dental x-ray machine wherein an x-ray source-camera assembly orbits a patient seated thereinbetween. A slot in the camera assembly collimates the x-rays which are continuously generated by the x-ray source, which x-rays are converted to light images of the patient's dental arch structure by only a single intensifying screen which remains stationary. This screen comprises about 1/40 the area of conventional intensifying screens and is made thicker for providing improved detection efficiency. A fiber optic minifying lens reduces the size of the image from the screen while proportionately increasing the light intensity of the image, thus making it possible to provide useable film images at reduced x-ray exposures due to non-linear film exposure versus optical density characteristics. The resultant minified, light-intensified image may now be recorded on 35 mm roll film, for example, as opposed to standard radiographic film of 5"×12" size, or 12.70 cm×30.48 cm.

2 Claims, 5 Drawing Figures

PANORAMIC DENTAL RADIOGRAPHY IMAGE INTENSIFICATION EMPLOYING MINIFICATION TECHNIQUES

STATEMENT OF THE INVENTION

This invention relates to panoramic dental radiography and more particularly concerns intensification of dental images through improved minification techniques.

BACKGROUND AND SUMMARY OF THE INVENTION

Prior art panoramic dental x-ray machines are well known. They include, among others, various structures and mechanisms for orbiting an x-ray source-x-ray film (tubehead-camera) assembly in circular or arcuate paths around the patient's head; for varying film travel speed in accordance with tubehead-camera assembly movements; for shifting the patient in a chair; and for providing continuous or discontinuous type radiographic images. Such structures and mechanisms are disclosed, for example, in U.S. Pat. Nos. 2,798,958; 3,045,118; 3,636,349; and 4,125,774.

Prior art systems require the x-ray film to be sandwiched between conventional intensifying screens, i.e., a double screen and double emulsion film, which screens permit the x-ray film to obtain the image in a shorter period of time and with less x-ray exposure to the patient. These double intensifying screens, with film therein between, move as a unit past a slot disposed centrally in a front panel of the camera. The intensifying screens are large, i.e., about 5"×12", or 12.70 cm×30.48 cm, are expensive and reusable but are easily damaged. For example, cracks, fissures and embedded dirt in the screens provide false images, as do bent screens; electrostatic charges which have developed on screen surfaces create lightning-like patterns on the radiograph and the like.

The present invention employs a single screen and single emulsion film although a double emulsion film may be used. The single screen is significantly smaller in area than the conventional prior art screens, having an active area only about 1/40 in the area thereof. Since the present screen is never flexed, it can be made substantially thicker, resulting in improved detection efficiency.

Intensifying screens are standard items which are commercially available. They fluoresce to emit visible light when struck by x-rays because of substances called phosphors contained within the screen. Each phosphor crystal that absorbs x-ray energy typically emits a bluish-green light whose brightness is related directly to the intensity of the x-rays in that infinitesimally small portion of the image. Thus, over the entire surface of the intensifying screen, differences in x-ray intensity are transformed into differences in light intensity to which the x-ray film is highly sensitive. The entire image is thus "intensified" for recording by the film. Consequently, smaller radiation doses are employed than would be needed without the screens. By increasing the thickness of the screen, as in the present invention, which increases the number of phosphor crystals, detection efficiency increases on the order of about 2 to 1, which increase in efficiency is offset by a loss thereof when only a single screen is used.

A minification lens is mounted after the screen, which lens reduces the panoramic images from the screen while concomitantly increasing the light intensity of the image. The reduced or minified light-intensified images are then recorded on 35 mm roll film, for example. By reducing the film size from the conventional 5"×12", or 12.70 cm×30.48 cm, of 35 mm film size, i.e., about a 14 to 1 reduction in size, which reduction is readily achievable through the practice of the present invention, there will result a savings in silver and film costs along with space required for film and screen storage. The size of the camera may be substantially reduced, not only because of the smaller size film contained therewithin, but the screen will have an input face of only about 5⅛"×0.275", or 13.02 cm×0.70 cm, which approximates the dimensions of the camera slot, as opposed to conventional 5"×12", or 12.70 cm×30.48 cm screens. Additionally, the size of the x-ray tubehead and its power supply may be substantially reduced.

The minification lens will typically comprise a fiber optic minification lens, conduit, or plate. The minified, light-intensified images are then recorded on film and subsequently magnified for inspection and/or diagnosis. As later explained, the invention offers up to about 10 to 1 dose reduction and a potential of up to about 7 to 1 image intensification.

DETAILED DESCRIPTION OF THE INVENTION

Figure 1:
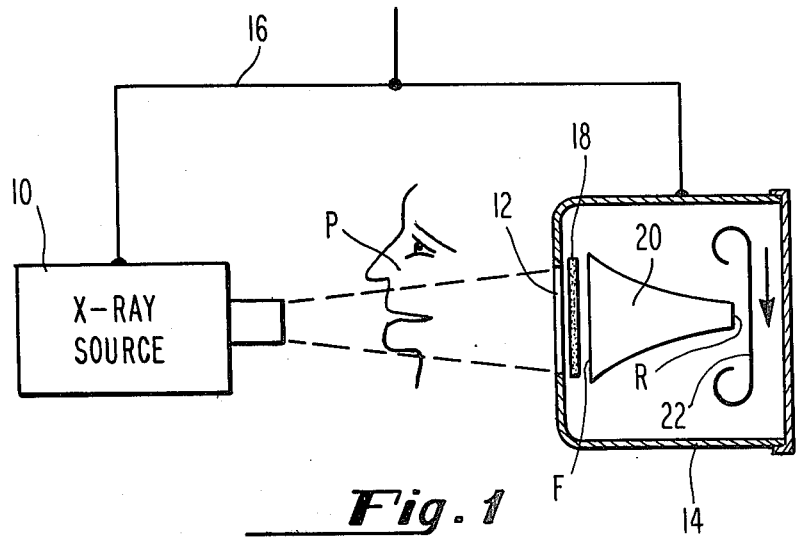
FIG. 1 is a diagrammatic illustration, partially in section, of apparatus for providing and recording minified panoramic central x-ray images.

In FIG. 1, an x-ray source 10 and camera slot 12 are optically aligned, the latter centrally disposed in a front panel plate of camera 14. Camera 14 and x-ray source 10 are supported on an arm 16 which rotates above the head of seated patient P situated in the path of x-ray beams generated by source 10 for collimation by slot 12. The patient may remain stationary or be transported in a patient chair in accordance with various type known drive patterns in order to simulate the generally elliptical shape of the human dental arch; to obtain continuous or discontinuous type images and the like.

A single intensifying screen 18, fiber optic minifying lens 20, and film 22, are disposed after slot 12 in the abovementioned sequence and are aligned therewith to travel as a unit within camera 14 in fixed, rotating relationship opposite source 10.

Typical x-ray sources and power supplies therefor of the assignee for use with their current panoramic dental x-ray machines are capable of generating a continuous series of x-ray pulses for producing panoramic radiographs of approximately 5"×12", or 12.70 cm×30.48 cm. The x-rays are generated by about 50 to 90 kVp at 5 mA for about 20 seconds duration which are applied to a half-wave self-rectified tungsten anode x-ray tube. X-ray source 10 of the present invention, assuming about a 10 to 1 reduction of the image by minification lens 20, typically requires 50 to 90 kVp at 0.5 mA for the same duration.

The single intensifying screen 18 is made thicker than conventional screens, as aforediscussed, for improved detection efficiency. Screen 18 is stationary and may be flush-mounted against slot 12. Screen 18 has an input face having dimensions approximating the dimensions of slot 12, i.e., about $5\frac{1}{8}''\times0.275''$, or 13.02 cm×0.70 cm, or slightly larger.

Figure 2:
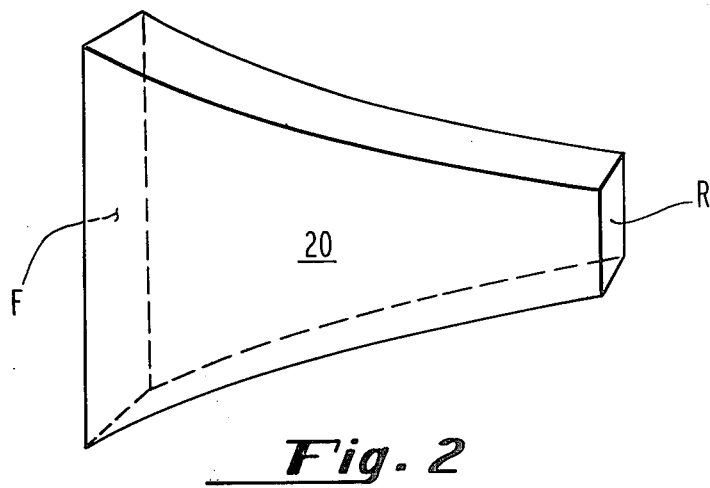
FIG. 2 is a perspective view, partially in phantom, of the minification lens of FIG. 1.

Lens 20 is preferably a fiber optic minifying lens and reduces the size of the image leaving screen 18. The degree of minification produced by lens 20 is determined by the ratio of areas of front face F and rear face R (FIG. 2). Front face F will have dimensions similar to slot 12 or screen 18, perhaps slightly larger, while rear face R measures approximately $1\frac{1}{4}''\times1/16''$, or 3.18 cm×0.16 cm. The ratio of areas of faces F and R is thus approximately 14 to 1. Consequently, the light intensity at rear face R is increased about 14 fold.

It should be noted, that although the input face or front face F of lens 20 and its output face or rear face R are spaced from screen 18 and film 22 respectively, it is preferred that contact, or very close proximal relationship exist in order to maximize light transfer efficiency.

Film 22 may be 35 mm roll film which can be driven at a varying speed by existing or known film drive mechanisms, but at a reduced speed. If, for example, the image is minified 10 fold, the speed of the film travel will be reduced by a factor equivalent to the square root of 10. If a 14 to 1 area minification is employed, as abovediscussed, then the standard 12.70 cm×30.48 cm radiograph may be reduced in size to 1.75"×3.12" (5.45 cm×7.92 cm) or a 35 mm film strip having a length of about 3.2" (8.13 cm). Such film strip may form a specified length of a longer length film strip; may comprise an individual strip of specified length depending upon the overall packaging and storage scheme desired; or may be individually cut film for convenience. Instant development film may also be used. Also, multiple images may be placed on wider film, i.e., along the bottom of the film, for example, and then by reversing the film strip, to record along the top, and the like.

In operation, x-rays generated by source 10 pass through dental arch area of patient P where the x-rays are attenuated in proportion to the density of the patient structure x-rayed. The attenuated x-rays pass through collimating slot 12 onto detector screen 18 which converts the attenuated x-rays to light images which enter front face F of minifying lens 20. Lens 20 reduces the size of the light image with a proportionate increase in light intensity, which minified light-intensified images are recorded on film 22.

Figure 3:
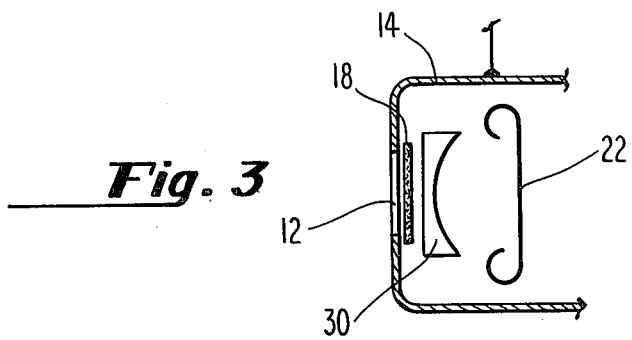
FIG. 3 is a view of the camera assembly of FIG. 1 showing another embodiment of the minification means.

Although a fiber optic minifying lens is preferred, a conventional optical reducing lens may be substituted therefor as shown in FIG. 3.

Figure 4:
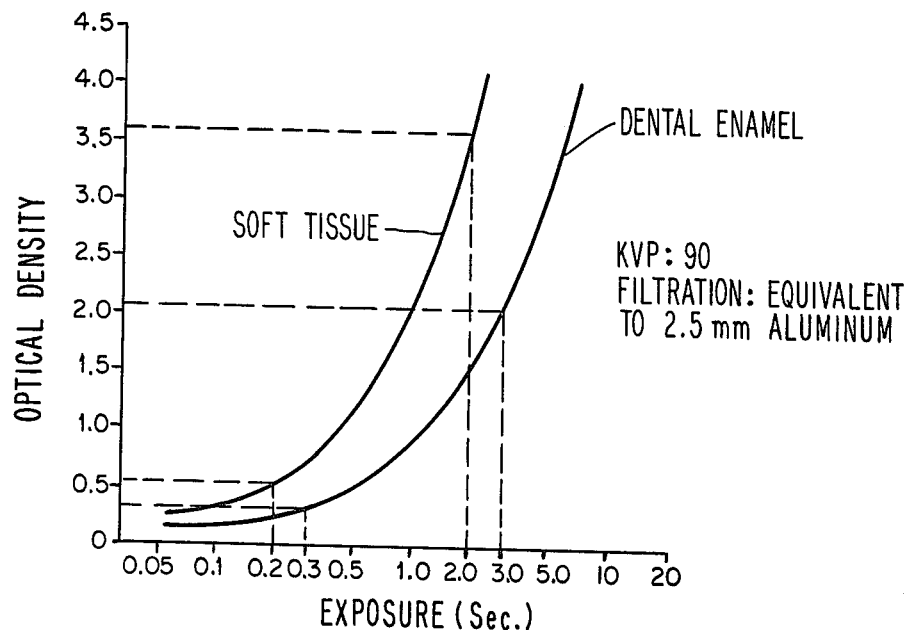
FIG. 4 graphically represents optical density of radiographic images of dental enamel and soft tissue plotted as a function of exposure time.

FIG. 4 illustrates typical curves where optical densities of radiographic images of dental enamel and soft tissue are plotted against time of exposure. If the slopes of the illustrated curves provide a reasonable indication of diagnostic potential, as suggested by Webber and Ryge in *Oral Surgery, Oral Medicine, and Oral Pathology,* Vol. 27, No. 6, pages 740-753, June, 1969, that portion of the curve above about density of 2.0, or where slopes are at a maximum, will be most informative.

The present invention utilizes the diagnostic potential of the upper portion of the curves, or that portion representing maximum slope. For example, through enamel, at an exposure time of 0.3 seconds, an optical density of about 0.3 results using an X-ray power supply of about 90 kVp and filtration equivalent to 2.3 mm of aluminum (FIG. 4). If the image is now minified in accordance with the present invention, such that the area of the image is reduced by only about 10 to 1, for example, the resultant light intensity of the image is increased by about the same ratio (assuming that the increase in exposure time can be equated to an increase in intensity), then a 3 second exposure will provide an optical density of 2.1, which represents about a 7 to 1 density increase. Stated differently, the present invention offers a potential of up to about 7 to 1 image intensification which is accomplished without the need for any electronic equipment and permits, for example, a 0.3 second exposure in lieu of a 3.0 second exposure to provide substantially equivalent radiographs of enamel.

Through soft tissue, at 0.2 and 2.0 seconds exposure, about 6 to 1 density increase or image intensification results using the same kVp and filtration equivalent as abovementioned. Thus, the invention permits a 0.2 second exposure, for example, in lieu of a 2.0 second exposure to provide substantially equivalent radiographs of soft tissue. It is appreciated that the exposure time values above presented are a function of film exposure characteristics and will vary in accordance therewith.

As aforementioned, since the dosage to the patient may now be reduced, a substantial reduction in the size of the tubehead and its power supply may readily be effected.

Detection efficiency of current intensifying screens is estimated to approach 50%. By increasing its thickness, detection efficiency is improved, coupled with a substantial increase in light intensity of the minified image. Any increase in light intensity above about a 2:1 ratio, i.e., above about 100%, increase quantum mottle or flicker on the film. Experience with microchannel plates and proximity focused diodes has demonstrated that a practical and useful gain may be low, i.e., not greater than about 50-100 to 1. Such gains provide light intensities on the film well above the film's minimum detection level, at the expense of additional mottle or flicker. The additional mottle or flicker produced by the increased light intensity of the image at rear face R of lens 20 can be less than the mottle or flicker produced by the aforementioned microchannel plates and proximity focused diodes due to their excessive gains and is tolerable and readily withstood without detracting noticeably from the diagnostic usefulness of the resultant images.

It is appreciated that microchannel plates are capable of providing gains in the millions. Proximity focused diodes provide lower gains, but are large and relatively complex. Both devices are comparatively expensive and would significantly increase cost to the user.

Current panoramic dental x-ray machines of the present assignee typically provide radiographs having 3 to 4 line pairs/mm resolution. Currently available x-ray film provide static resolutions greater than this or about 10 line pairs/mm when associated with present day intensifying screens. A 10 to 1 reduction, for example, of the image in accordance with the present invention, provides about a 10 fold increase in the light intensity of the minified image, which still yields a static resolution of about 10 line pairs/mm on the film. If the image is remagnified to its original size, i.e., as portrayed on the 5"×12", or 12.70 cm×30.48 cm radiograph, then the resultant resolution would be obtained by dividing the square root of 10, or 3 1/6, into 10 line pairs/mm, resulting in 3-4 line pairs/mm achievable on current machines of the assignee, as stated above. Reducing the image size 10 fold also makes it possible to reduce the power to the X-ray source, by about 2 to 1 for example, while yet permitting the speed of rotation of the tubehead-camera assembly around the patient's head to be reduced, for example, by about 5 to 1. Other ratios may be considered, for example, such as a 10:1 power reduction with no concomitant change in speed of rotation.

Figure 5:
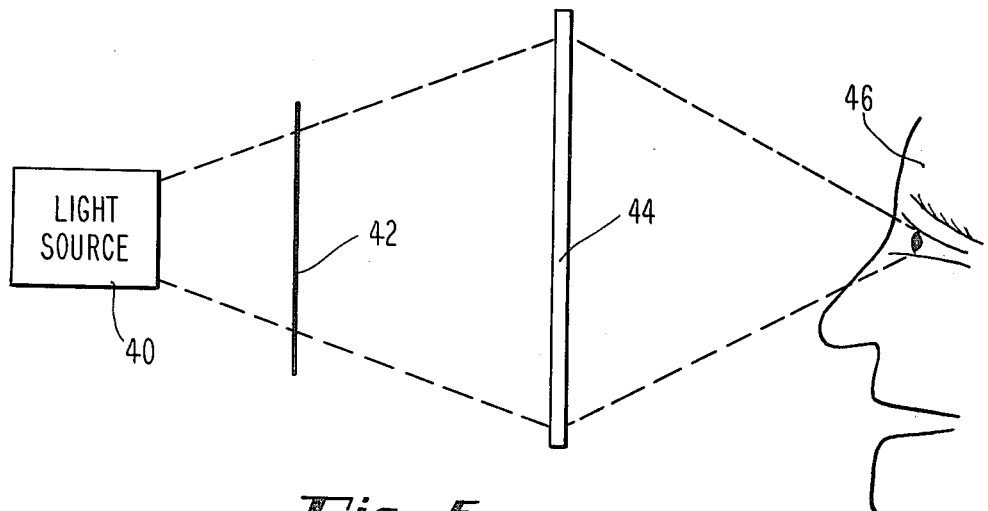
FIG. 5 diagrammatically illustrates apparatus for magnifying the processed film for diagnostic viewing.

For inspection or diagnostic analysis of the processed film, reference is made to FIG. 5. A suitable light source 40 or projector projects light beams through the processed film 42, the images thereon being displayed on a suitable display screen 44 for viewing by diagnostician 46. The projected image size is preferably approximately 5"×12", or 12.70 mm×30.48 mm, the size of a standard radiograph, although the projected image may readily be magnified above life size to diagnostic advantage.

The minified images on the film can be projected or enlarged to full size with little loss of the image information. Comparing the present system which employs minification techniques with conventional x-ray systems, the former provides approximately a 7 fold increase in density of the image on the film for the same input x-ray signal, or approximately the same density of the image on the film for an x-ray signal having 1/10 the signal.

I claim:

1. An x-ray machine comprising an x-ray source adapted to continuously direct x-radiation through a slot provided in a front panel of a camera assembly containing film controllably movable therewithin for exposing selected portions thereof to x-radiation passing through a patient disposed between said x-ray source and camera assembly to form images of said patient on said film, said x-ray source and said camera assembly orbiting as a unit about head of said patient, said machine comprising intensifying means mounted within said camera assembly immediately after said slot to receive all x-radiations passing therethrough for conversion thereof into light images, said intensifying means comprising a single stationary intensifying screen, input face and output face of said intensifying screen being substantially identical in size with said slot, minifying means mounted within said camera assembly after said intensifying means for receiving said light images from said intensifying means for reducing said light images in size into minified images having increased intensity, said minifying means comprising a fiber optic minifying lens having input face greater in area than its output face, said lens input face having dimensions substantially identical with said input and output faces of said intensifying screen, said input face of said lens being mounted in very close operable proximity to said output face of said intensifying screen, said lens output face having dimensions to provide a ratio of lens input face to lens output face of about 14 to 1, and wherein light intensity of said image leaving said output face of said minification lens has a light intensity at least 10 fold greater than light intensity of image leaving said intensifying screen, and wherein optical density of a radiographic image of dental enamel obtained through said minification lens which provides a light intensity at its output face at least 10 fold greater than light intensity of image leaving said intensifying screen represents about a 7 to 1 optical density increase when exposure time is set at about 0.3 seconds using an x-ray power supply of about 90 kVp and filtration equivalent to 2.5 mm of aluminum, and said optical density of said radiographic image of said dental enamel is about 0.3, and wherein said 7 to 1 optical density increase represents a potential of about 10 to 1 dose reduction.

2. An x-ray machine comprising an x-ray source adapted to continuously direct x-radiation through a slot provided in a front panel of a camera assembly containing film controllably movable therewithin for exposing selected portions thereof to x-radiation passing through a patient disposed between said x-ray source and camera assembly to form images of said patient on said film, said x-ray source and said camera assembly orbiting as a unit about head of said patient, said machine comprising intensifying means mounted within said camera assembly immediately after said slot to receive all x-radiations passing therethrough for conversion thereof into light images, said intensifying means comprising a single stationary intensifying screen, input face and output face of said intensifying screen being substantially identical in size with said slot, minifying means mounted within said camera assembly after said intensifying means for receiving said light images from said intensifying means for reducing said light images in size into minified images having increased intensity, said minifying means comprising a fiber optic minifying lens having input face greater in area than its output face, said lens input face having dimensions substantially identical with said input and output faces of said intensifying screen, said input face of said lens being mounted in very close operable proximity to said output face of said intensifying screen, said lens output face having dimensions to provide a ratio of lens input face to lens output face of about 14 to 1, and wherein light intensity of said image leaving said output face of said minification lens has a light intensity at least 10 fold greater than light intensity of image leaving said intensifying screen, and wherein optical density of a radiographic image of dental soft tissue obtained through said minification lens which provides a light intensity at its output face at least 10 fold greater than light intensity of image leaving said intensifying screen represents about a 6 to 1 optical density increase when exposure time is set at about 0.2 seconds using an x-ray power supply of about 90 kVp and filtration equivalent to 2.5 mm of aluminum, and said optical density of said radiographic image of said dental soft tissue is about 0.6, and wherein said 6 to 1 optical density increase represents a potential of about 10 to 1 dose reduction.

* * * * *